United States Patent [19]

Bach

[11] Patent Number: 4,647,539
[45] Date of Patent: Mar. 3, 1987

[54] METHOD AND APPARATUS FOR GROWING CELLS IN VITRO

[75] Inventor: Bert R. Bach, Minneapolis, Minn.

[73] Assignee: Endotronics, Inc., Coon Rapids, Minn.

[21] Appl. No.: 737,515

[22] Filed: May 24, 1985

[51] Int. Cl.$^4$ .................................................. C12M 3/00
[52] U.S. Cl. ................................ 435/284; 210/321.3; 435/240
[58] Field of Search ............... 435/284, 285, 286, 240; 210/321.1, 321.2, 321.3, 321.4

[56] References Cited

U.S. PATENT DOCUMENTS

| | | | |
|---|---|---|---|
| 3,407,120 | 10/1968 | Weiss et al. | 195/104 |
| 3,598,728 | 8/1971 | Bixler et al. | 210/22 |
| 3,734,851 | 5/1973 | Matsumura | 210/22 |
| 3,767,790 | 10/1973 | Guttag | 424/81 |
| 3,821,087 | 6/1974 | Knazek et al. | 195/127 |
| 3,827,565 | 8/1974 | Matsumura | 210/22 |
| 3,883,393 | 5/1975 | Knazek et al. | 195/1.8 |
| 3,911,140 | 10/1975 | Osborne et al. | 426/36 |
| 3,997,396 | 12/1976 | Delente | 195/1.8 |
| 4,087,327 | 5/1978 | Feder et al. | 195/1.7 |
| 4,181,604 | 1/1980 | Onishi et al. | 210/8 |
| 4,184,922 | 1/1980 | Knazek et al. | 435/284 |
| 4,200,689 | 4/1980 | Knazek et al. | 435/2 |
| 4,201,845 | 5/1980 | Feder et al. | 195/127 |
| 4,206,015 | 6/1980 | Knazek et al. | 435/2 |
| 4,219,426 | 8/1980 | Spekle et al. | 210/321.3 X |
| 4,220,725 | 9/1980 | Knazek et al. | 435/285 |
| 4,242,460 | 12/1980 | Chick et al. | 435/284 |
| 4,271,014 | 6/1981 | Aid et al. | 210/321.3 X |
| 4,283,284 | 8/1981 | Schnell | 210/321.3 |
| 4,334,993 | 6/1982 | Norton | 210/321.3 |
| 4,374,802 | 2/1983 | Fukasawa | 210/321.3 X |
| 4,377,639 | 3/1983 | Lee | 435/285 |
| 4,391,912 | 7/1983 | Yoshida et al. | 435/241 |
| 4,396,510 | 8/1983 | Hsei | 210/321.3 |
| 4,440,853 | 4/1984 | Michaels et al. | 435/68 |
| 4,442,206 | 4/1984 | Michaels et al. | 435/68 |
| 4,517,720 | 5/1985 | Otstot et al. | 210/321.1 X |

*Primary Examiner*—Margaret A. Focarino
*Attorney, Agent, or Firm*—Kinney & Lange

[57] ABSTRACT

The present invention includes a cell culture apparatus for growing and maintaining living cells in vitro. The cell culture apparatus includes a shell being at least partially constructed of a flexible material. A plurality of capillaries are disposed within the shell, defining a cell culturing space between the capillaries and the shell wall. At least one of the capillaries has selectively permeable walls. The shell permits one end of the apparatus to be moved towards another end, spreading apart the capillaries.

31 Claims, 7 Drawing Figures

METHOD AND APPARATUS FOR GROWING CELLS IN VITRO

BACKGROUND OF THE INVENTION

1. Field of the Invention

The present invention relates to a hollow fiber apparatus for culturing cells and to a method of using the apparatus to grow and maintain living cells in vitro.

2. Description of the Prior Art

Various hollow fiber apparatus have been used to grow and maintain living cells in vitro. These apparatus typically include a hollow shell with a plurality of semi-porous hollow fiber membranes extending through shell. A fluid medium containing oxygen, nutrients and other chemical stimuli is circulated through the lumen of the hollow fiber membranes. Cells are seeded in an extracapillary fluid space between the fiber membranes and the shell wall. The oxygen, nutrients and other chemical stimuli diffuse through the semi-porous walls of the hollow fiber membranes into the extracapillary space to maintain and stimulate the growth of the cells. Simultaneously, waste products and contaminating proteins diffuse from the extracapillary space through the walls and into the lumen of the hollow fibers, and are carried away by the fluid medium. The cell culture device of U.S. Pat. No. 3,821,087 to Knazek et al. is representative of this type of cell culture device, and U.S. Pat. No. 3,883,393 to Knazek et al. and U.S. Pat. No. 4,391,912 to Yoshida et al. generally describe a method of using such an apparatus.

To economically produce cell derived products in a hollow fiber culture device, a large number of cells must be maintained viable in optimal culture conditions for product formation over long periods of time. Prior art hollow fiber culture devices, such as disclosed in U.S. Pat. No. 3,821,087 to Knazek et al., have many limitations that prevent their use in the economical production of cell derived products in commercial quantities. One limitation of these prior art hollow fiber culture devices is that the fibers frequently stick together and reduce the surface area to which the cells may attach. Also, the fibers are not equidistantly spaced in the cell culture device. As the cells grow and the cell density increases, it becomes more difficult for the nutrients, oxygen and other chemical stimuli to diffuse through the walls of the hollow fiber membranes and through the layers of cells that have developed to reach remote cells (cells which are the furthest away from the fiber membranes) and for waste material produced by the remote cells to diffuse back into the lumen of the hollow fiber membranes. This results in anoxic or dead spaces. Cells located within these spaces will die due to the lack of oxygen or failure of nutrients to reach the cells by diffusion.

Another limitation is that very little fluid motion occurs in the cell compartment. Limited fluid motion in the cell compartment (extracapillary space) leads to micro environments forming around quickly metabolizing cells, adversely affecting other cells in the cell culture apparatus by altering PH.

The present invention is designed to overcome these limitations.

SUMMARY OF THE INVENTION

The present invention includes an improvement in a cell culturing apparatus and a method of using the improved cell culturing apparatus for growing and maintaining living cells in vitro. The cell culturing apparatus includes a flexible container having an inner chamber. A plurality of capillaries are disposed within the chamber of the container, dividing the chamber into an intracapillary space (the lumen of the hollow capillaries) and an extracapillary space between the capillaries and the wall of the container. At least one of the capillaries has selectively permeable walls, and the intracapillary and extracapillary spaces communicate with each other only through the walls of the capillaries. The manner in which the capillaries are secured to the container and the flexibility of the container permit manipulation of the configuration of the container to separate the capillaries from each other within the chamber of the container.

In use, cells are implanted in the extracapillary space. A fluid medium carrying nutrients, oxygen and other chemical stimuli is circulated through the intracapillary space. Simultaneously, the container is manipulated so that the capillaries generally move away from each other. Separation of the capillaries within the chamber enhances the transfer of nutrients, oxygen, and other chemical stimuli from the intracapillary space to the extracapillary space and the transfer of waste products from the extracapillary space to the intracapillary space.

DETAILED DESCRIPTION OF THE PREFERRED EMBODIMENTS

Figure 1:
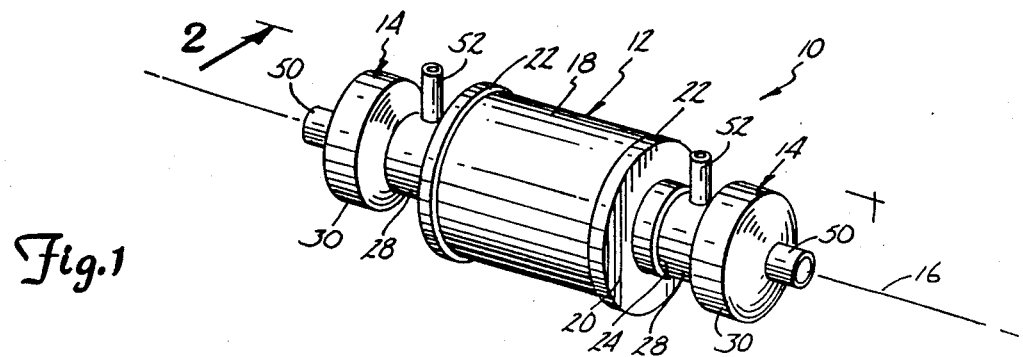
FIG. 1 is a perspective view of one preferred embodiment of the cell culture apparatus of the present invention.

A preferred embodiment of a cell culture apparatus of the present invention, used to grow living cells in vitro in a sterilized environment, is generally indicated at 10 in FIG. 1. The cell culture apparatus includes a flexible hollow container or shell which includes a middle segment 12 carried between two end segments 14 in axial alignment along a longitudinal axis 16. At least one of the segments, and preferably the middle segment 12, is at least partially constructed of a flexible material such as silicon rubber.

Figure 2:
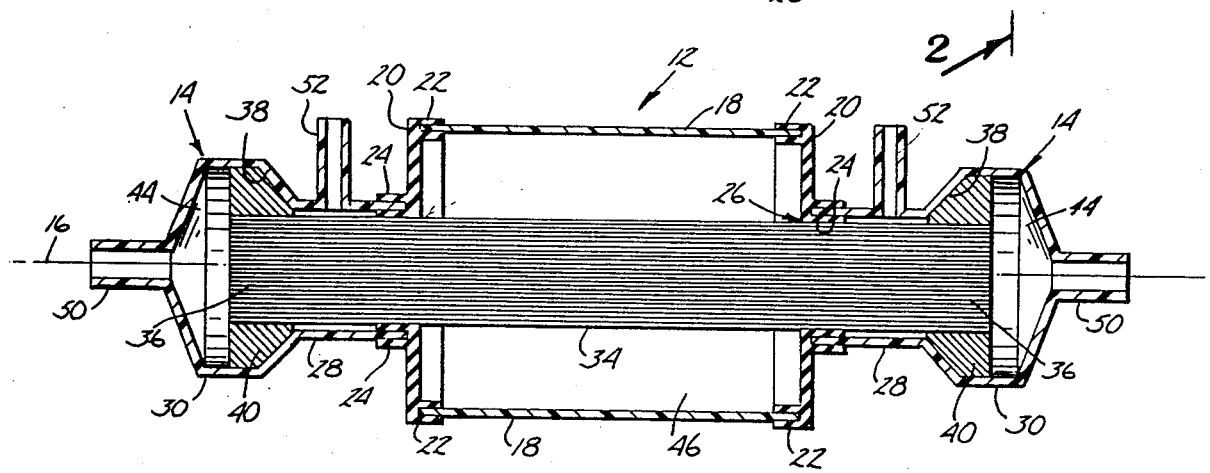
FIG. 2 is a longitudinal cross sectional view of the cell culture apparatus of the present invention taken along the line 2—2 of FIG. 1, illustrating a plurality of capillaries disposed in a normal position within an inner chamber defined by a container of the present invention.

As shown in FIG. 2, the middle segment 12 includes a rigid, preferably transparent plastic tube 18 of circular lateral cross section, and a pair of flexible annular end flanges 20 defining the longitudinal ends of the middle segment 12. The end flanges 20 are secured adjacent an outer edge 22 to the tube 18 forming a fluid seal. Inner edges 24 of the end flanges 20 define passages 26 to the interior of the middle segment 12, which passages 26 are aligned along the longitudinal axis 16 of the container.

The end segments 14 have a substantially tubular first end 28 of circular lateral cross section, which first ends 28 are secured to the inner edges 24 of the annular flanges 22 forming a fluid seal. The end segments 14 further preferably include a hollow, generally bulb-shaped end portion 30, having a lateral cross section of greater dimension than the lateral cross section of the first end 28. Other end segment configurations are within the scope of the present invention.

A plurality of capillaries 34 are disposed within the container in a normal position preferably substantially parallel to and symmetrically disposed about the longitudinal axis 16 of the container, as shown in FIG. 2. Capillaries 34 have end portions 36 which extend into the bulb-shaped end portion 30 of end segments 14, and are potted within inner walls 38 of the end segments 14 by a potting compound 40, such as a polyurethane or an RTV silicone polymer.

The potting compound 40 divides the interior of the container into two oppositely disposed end chambers 44 in fluid communication with the lumens or "intracapillary space" of the capillaries 34 and a central chamber 46 in communication with an "extracapillary" space between the capillaries 34 and the walls of the container. Potting compound 40 prevents direct communication between end chambers 44 and central chamber 46 so that fluid must flow through the capillaries 34. As shown in FIG. 2, end chambers 44 are defined at the longitudinal extremities of the container and occupy that portion of the space within the bulb-shaped end portion 30 of end segments 14 not occupied by the potting compound 40. Central chamber 46 includes the interior of the middle segment 12 and the interior of the first ends 28 of end segments 14.

At least one, and preferably all, of the capillaries 34 have semi-porous, selectively permeable walls to permit the extracapillary space and intracapillary space to communicate through the walls of the capillaries 34. The capillaries 34 are preferably constructed from a membrane material compatible with the cell line being cultured. Materials used in making the capillaries include cellulose acetate, polysulfone, and acrylic copolymers.

Extending axially outwardly from the second ends 30 of the end segments 14, are a first set of tubular ports 50. Ports 50 fluidly communicate with the end chambers 44 and the lumens of the capillaries 34, for circulating a first fluid medium therethrough. This first fluid medium includes nutrients, oxygen and other chemical stimuli for enhancing and maintaining cell growth in the cell chamber or extracapillary space. A second set of tubular ports 52 extend outwardly from the first ends 28 of the end segments 14, in substantially perpendicular alignment with the longitudinal axis 16 of the container. Tubular ports 52 communicate with the extracapillary space of the central chamber 46, for circulating a second fluid medium therethrough and for implanting cells into the extracapillary space.

Figure 3:
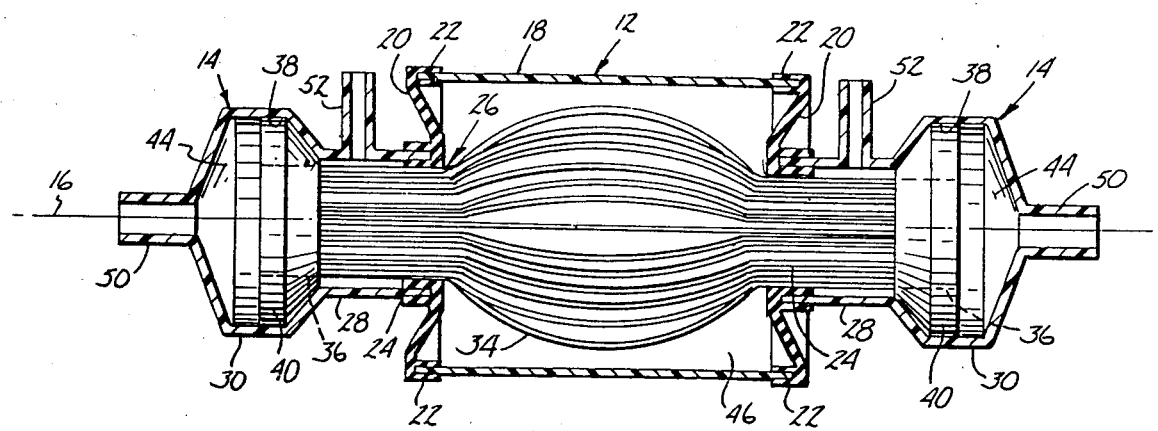
FIG. 3 is a longitudinal cross sectional view similar to FIG. 2, illustrating the cell culture apparatus of the present invention with the configuration of the container distorted to spread apart the capillaries with respect to each other within the inner chamber of the container.

The flexibility of the annular end flanges 20 allows the end segments 14 to be linearly and/or angularly moved with respect to each other and the middle segment 12. Because the end portions 36 of capillaries 34 are secured to the end segments 14 by potting compound 40, movement of the end segments 14 with respect to each other causes the capillaries 34 to move out of their normal position within the central chamber 46, and away from each other. Nutrients, oxygen and other chemical stimuli carried by the first fluid medium are better able to reach all of the cells since the distance from a "remote" cell to a capillary has been reduced, and waste products in the extracapillary space more readily diffuse due to the repositioning of the capillaries 34. Also, repetitive movement of the capillaries agitates the second fluid medium to increase fluid motion in the extracapillary space. In FIG. 3, the end segments 14 have been moved linearly along the longitudinal axis 16 towards each other, causing the capillaries 34 to fan out, moving substantially radially away from the longitudinal axis 16 of the container and away from each other. When capillaries 34 are moved apart the distance from a "remote" cell to the nearest capillary (nutrient source) is reduced, reducing the travel distance of nutrients from the capillary to the cell and the travel distance of waste product from the cell to the capillary.

A Silicone polymer is a preferred flexible material because it is inert, having no affect on living cells. A transparent plastic, such as polycarbonate, which is also substantially inert, is a preferred material for those portions of the apparatus 10 which are intended to be rigid. A transparent plastic permits observation of the cell growth and movement of the capillaries 34 within the central chamber 46 of the container. It should be noted that although middle segment 12 is depicted with a rigid tube 18 and flexible annular end flanges 20, any portion of the middle segment 12 or the end segments 14 may be constructed of flexible material so long as the container can be distorted to cause movement of the capillaries 34 within the central chamber 46.

Figure 4:
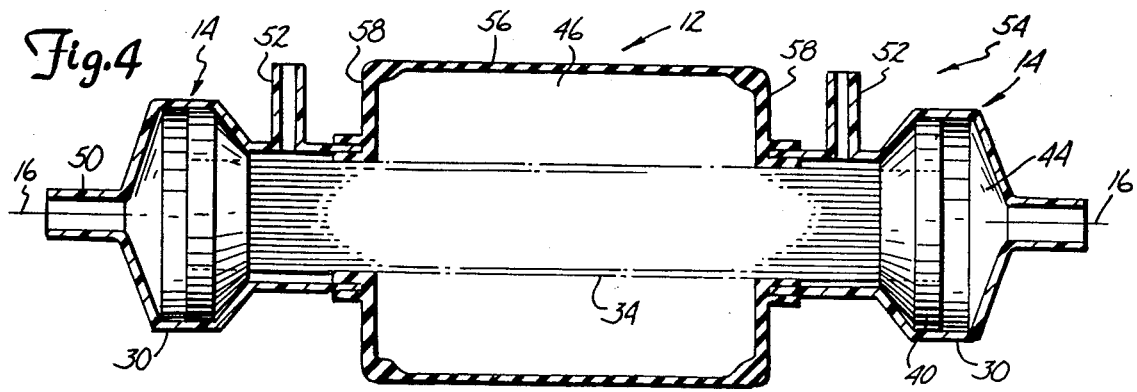
FIG. 4 is a longitudinal cross sectional view, similar to FIG. 2, of an alternative embodiment of the cell culture apparatus of the present invention in a normal configuration.
Figure 5:
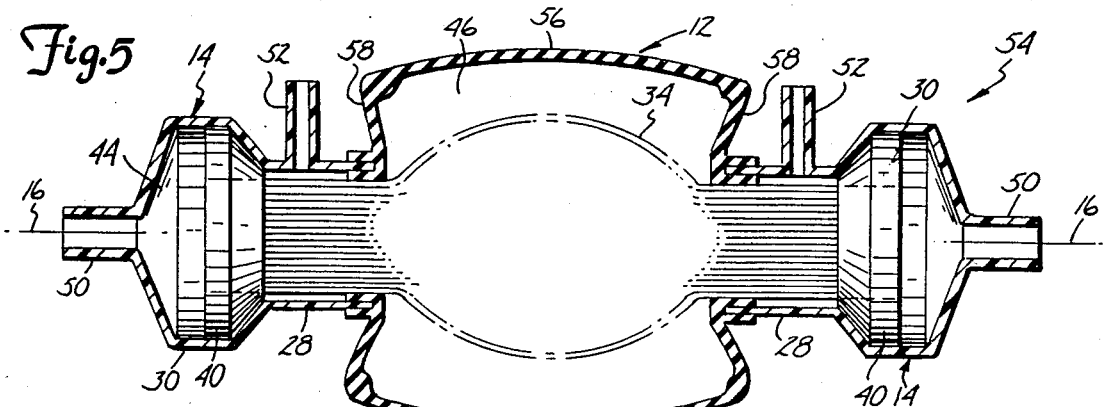
FIG. 5 is a longitudinal cross sectional view of the alternative embodiment of FIG. 4 of the cell culture apparatus of the present invention with the configuration of the container distorted to spread apart the capillaries with respect to each other within the inner chamber of the container.

A second alternative embodiment of the apparatus of the present invention is generally indicated at 54 in FIGS. 4 and 5. In the second alternative embodiment 54, the middle segment 12 includes a flexible tubular wall 56 integrally formed with oppositely disposed, flexible, annular end flanges 58. Thus, middle segment 12 is a substantially integral cylindrical unit, having annular longitudinal end walls 58 on which the end segments 14 are secured to form a fluid seal. As shown in the cross sectional view of FIG. 5, the capillaries 34 are displaced from their normal position, substantially parallel to and symmetrically disposed around the longitudinal axis 16 of the container, as shown in FIG. 4, due to inward axial movement of the end segments 14 with respect to each other. The entirely flexible middle segment 12 enhances the flexibility of the container. To permit observation of the agitation process and to monitor the growth of cells in the extracapillary space, the middle segment 12 is constructed of a transparent or translucent material such as silicone rubber.

Although the capillaries 34 of the alternating embodiment 54 may be displaced from their normal position by any suitable means, two distinct methods are described for illustrative purposes. First, the end segments 14 may be mechanically linearly moved toward and away from each other along the longitudinal axis 16 of the apparatus 10, and/or be angularly moved with respect to each other around the longitudinal axis 16 of the container. Secondly, the fluid pressure within the lumens of the capillaries 34 and within the extracapillary space may be adjusted to manipulate the shape of the middle segment 12 of the container. In FIG. 5, the middle segment 12 is particularly designed to symmetrically, radially expand away from the longitudinal axis 16 of the container when a first fluid medium is delivered into the central chamber 46 at a pressure above the atmospheric pressure (or the "environmental" pressure within which the apparatus 10 is contained). The radial expansion of the middle segment 12 draws the end segments 14 toward each other along the longitudinal axis 16 of the container, causing displacement of the hollow capillaries 34 from their normal position within the chamber 46 and generally away from each other. Because a change in pressure between the extracapillary space and the intracapillary space may affect the diffusion rates of chemicals and substances between the intracapillary and extracapillary spaces, a second fluid medium is circulated through the lumens of the capillaries at a second selected pressure to control the diffusion rates.

Figure 6:
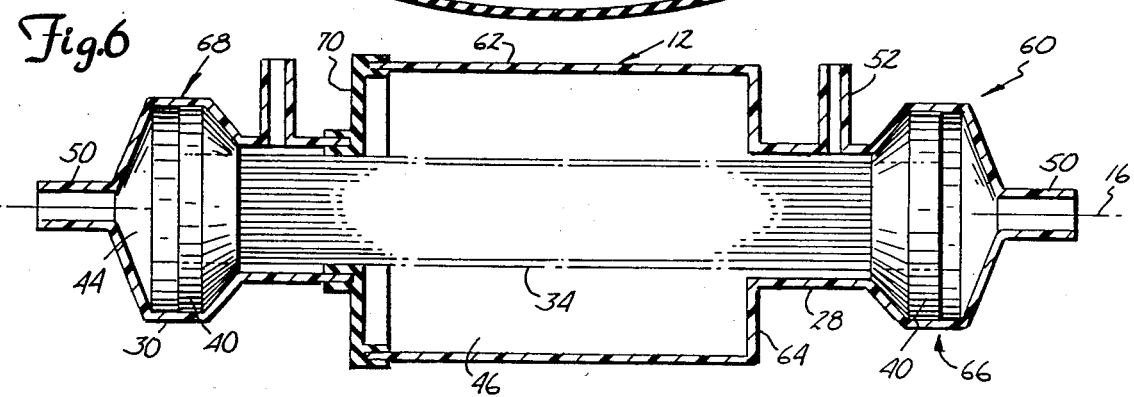
FIG. 6 is a longitudinal cross sectional view, similar to FIG. 2, of yet another alternative embodiment of the cell culture apparatus of the present invention in a normal configuration.
Figure 7:
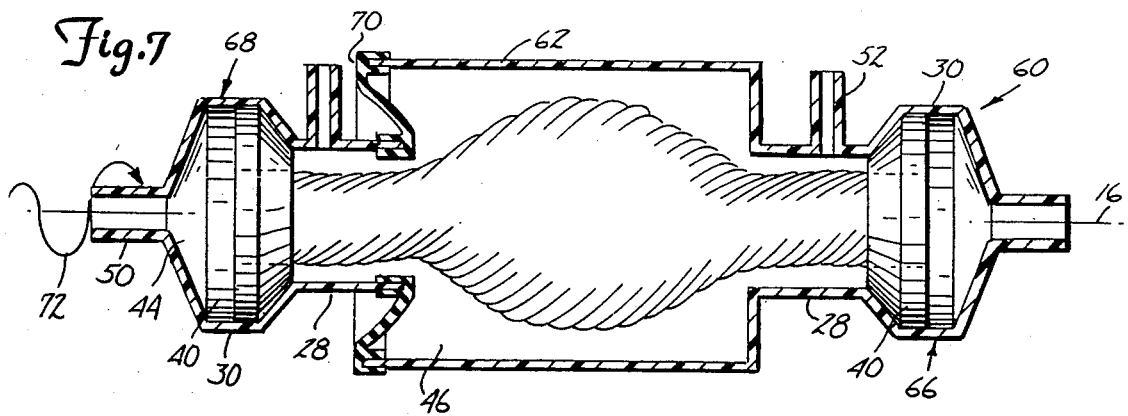
FIG. 7 is a longitudinal cross sectional view of the alternative embodiment of FIG. 7 of the cell culture apparatus of the present invention with the configuration of the container distorted to spread apart and twist the capillaries with respect to each other within the container.

A third alternative of the apparatus of the present invention is generally indicated at 60 in FIGS. 6 and 7. With the third alternative embodiment, the middle segment 12 includes a rigid, transparent plastic tube 62 having a circular lateral cross section. Preferably, the tube 62, an annular end wall 64, and a first end segment 66, are integrally formed of transparent plastic. The tube 62 is further secured to a second end segment 68 by a flexible, annular end flange 70. As illustrated in FIG. 7, second end segment 68 is simultaneously linearly moved toward and angularly rotated with respect to the first end segment 66 to displace the capillaries 34 from their normal position (shown in FIG. 6, substantially parallel to and symmetrically disposed around longitudinal axis 16) within the central chamber 46. The linear movement and angular rotation relative to the longitudinal axis 16 of the container, are indicated by direction arrow 72. This twists and fans the capillaries 34 away from each other within the central chamber 46 as shown in FIG. 7.

In use, the cells are implanted in the extracapillary space in a conventional manner such as through one of the ports 52. To ensure that all of the cells within the extracapillary space, as they multiply, receive an adequate supply of nutrients and that the waste products are removed sufficiently so that the cells grow and multiply the capillaries, the capillaries 34 are spread apart by moving the ends 14 towards each other as illustrated in FIGS. 3 and 5. Alternatively, the ends may be moved towards each other and twisted such as illustrated in FIG. 7. The ends are retained with the capillaries spread apart or twisted and spread apart by any suitable manner such as by being clamped using conventional clamping equipment.

In addition, the fluid in the extracapillary space may be agitated to increase nutrient availability and to increase removal of waste product by moving the ends of the apparatus of the present invention repetitively towards each other and away from each other. Care must be taken that the capillaries 34 do not cause too vigorous of an agitation of the fluid within the extracapillary space so that damage to the cells and the cell structures is avoided. The movement of the ends towards each other may be accomplished by moving both ends by a suitable motor and cam device (not shown) or by having one end fixed and moving the other by the same motor and camming device (not shown). The manner in which the ends of the apparatus of the present invention is moved is not particularly important to the present invention and other methods, specifically not described, are includable within the scope of the present invention.

Any combination of the features shown in the three described embodiments is anticipated by the present invention. Any of the three segments of the container, or any portions thereof, may be constructed of any suitable flexible material; capillaries 34 having a selected pore size may be attached to the container in any suitable manner and in any suitable place; and the container may be manipulated in any suitable manner which will separate the capillaries from each other within the central chamber 46 to improve the transfer of selected chemicals and substances between the intracapillary and extracapillary spaces through the walls of capillaries 34.

Although the present invention has been described with reference to preferred embodiments, workers skilled in the art will recognize that changes may be made in form and detail without departing from the spirit and scope of the invention.

What is claimed is:

1. An improved cell culture apparatus for in vitro cell growth, the apparatus including a shell having first and second end segments, a plurality of capillaries extending between the first and second end segments and a tubular wall extending therebetween, at least one of the capillaries having selectively permeable walls, a cell culturing space being defined between the capillaries and the tubular wall of the shell, and first and second ports attached to the shell in fluid communication with lumens of the capillaries, the improvement comprising:
   the tubular wAll having at least a portion thereof constructed of a material sufficiently flexible so that the capillaries are movable when at least one of the end segments is moved; and
   first means for securing the capillaries to the shell such that movement of one of the segments causes the capillaries to move within the shell.

2. The apparatus of claim 1 wherein the capillaries have end portions secured to the first and second end segments, and at least one of the segments is constructed of a flexible material.

3. The apparatus of claim 1 wherein at least one segment is non-flexible.

4. The apparatus of claim 1 wherein the tubular wall is constructed of a transparent material.

5. The apparatus of claim 2 wherein the one flexible segment is at least partially constructed of silicone rubber.

6. The apparatus of claim 1 wherein the tubular wall and the first and second end segments are disposed coaxially.

7. The apparatus of claim 1 wherein the capillaries are disposed within the shell in substantially parallel alignment with each other and a longitudinal axis of the shell.

8. The apparatus of claim 1 wherein the capillaries are symmetrically disposed around the longitudinal axis of the shell.

9. The apparatus of claim 1 wherein the first means for securing comprises a potting compound bonding the end portions of the capillaries to the first and second end segments of the shell.

10. The apparatus of claim 1 wherein:
the first and second end segments include a tubular first end of substantially circular cross-section; and
the tubular wall includes second means for securing the tube to the first ends of the first and second end segments.

11. The apparatus of claim 10 wherein the second means for securing comprises a pair of substantially annular flanges attached adjacent an outer edge to the tubular wall and attached adjacent an inner edge to the first ends of the first and second end segments.

12. The apparatus of claim 11 wherein at least one flange is flexible.

13. The apparatus of claim 11 wherein the tubular wall is flexible.

14. The apparatus of claim 12 wherein the tubular wall is constructed of transparent material.

15. The apparatus of claim 1 further comprising means for communicating with the cell culturing space.

16. The apparatus of claim 15 wherein the means for communicating comprises third and fourth ports carried by the end segments in fluid communication with the central chamber.

17. The apparatus of claim 1 wherein the fluid pressure within the cell culturing space and within the lumens of the capillaries is selectively adjustable and the shape of the shell changes in response to changes in the fluid pressure within the cell culture space and the lumens of the capillaries, causing movement of the capillaries within the shell.

18. The apparatus of claim 1 wherein the end segments are linearly movable with respect to each other along the longitudinal axis of the shell to move the capillaries within the shell with respect to each other.

19. The apparatus of claim 18 wherein linear movement of the end segments toward each other causes substantially radially outward movement of the capillaries with respect to the longitudinal axis of the shell.

20. The apparatus of claim 18 wherein the end segments are coincidentally linearly and angularly movable with respect to each other.

21. The apparatus of claim 20 wherein the end segments are linearly movable along and angularly movable about the longitudinal axis of the shell.

22. A method of enhancing the growth of living cells in vitro using a hollow fiber cell culture apparatus having a housing with a flexible section, the method comprising:
implanting cells within cell culture space of the cell culture apparatus; and
circulating a first fluid medium carrying nutrients through lumens of the hollow fibers; and
moving a first end of the cell culture apparatus to move the fibers with respect to each other.

23. The method of claim 22 and further including:
moving the first end toward and away from a second end in a repetitive manner.

24. The method of claim 23 wherein the first and second ends are moved towards each other in a repetitive manner.

25. The method of claim 22 wherein the first end is moved toward the second end of the shell and twisted angularly.

26. A cell culture apparatus for in vitro cell growth having a plurality of capillaries extending through a cell culturing space, the apparatus comprising:
a housing having first and second end segments and a tubular wall extending therebetween and the capillaries extending between the first and second end segments defining a cell culturing space between the capillaries and the tubular housing, the tubular housing having a portion constructed of a material sufficiently flexible so that the capillaries are movable with respect to each other when at least one of the end segments of the housing is moved.

27. The apparatus of claim 26 wherein the capillaries have end portions secured to the first and second end segments, and at least one of the end segments is constructed of a flexible material.

28. The apparatus of claim 26 wherein at least one end segment is non-flexible.

29. The apparatus of claim 26 wherein the tubular wall is constructed of a transparent material.

30. The apparatus of claim 29 wherein the one flexible segment is at least partially constructed of silicone rubber.

31. A cell culture apparatus comprising:
a housing having first and second ends and a tubular wall extending between the first and second ends and a plurality of capillaries extending and attached to the first and second ends and a cell culturing space defined between the housing and the capillaries, the tubular wall being attached to the first and second ends by first and second flanges, at least one of the flanges being made of a material sufficiently flexible to that the capillaries are movable with respect to each other during cell culturing.

* * * * *